(12) United States Patent
Nishio et al.

(10) Patent No.: US 9,535,003 B2
(45) Date of Patent: Jan. 3, 2017

(54) SPR SENSOR CELL AND SPR SENSOR

(71) Applicant: NITTO DENKO CORPORATION, Osaka (JP)

(72) Inventors: Hajime Nishio, Osaka (JP); Tomohiro Kontani, Osaka (JP)

(73) Assignee: NITTO DENKO CORPORATION, Ibaraki-shi (JP)

( * ) Notice: Subject to any disclaimer, the term of this patent is extended or adjusted under 35 U.S.C. 154(b) by 0 days.

(21) Appl. No.: 14/426,376

(22) PCT Filed: Aug. 30, 2013

(86) PCT No.: PCT/JP2013/073251
§ 371 (c)(1),
(2) Date: Mar. 5, 2015

(87) PCT Pub. No.: WO2014/038475
PCT Pub. Date: Mar. 13, 2014

(65) Prior Publication Data
US 2015/0260649 A1    Sep. 17, 2015

(30) Foreign Application Priority Data

Sep. 7, 2012   (JP) .................................. 2012-197178

(51) Int. Cl.
*G01N 21/552*    (2014.01)
*G01N 21/03*    (2006.01)
(Continued)

(52) U.S. Cl.
CPC ............ *G01N 21/553* (2013.01); *G01N 21/03* (2013.01); *G02B 6/10* (2013.01); *G02B 6/1226* (2013.01);
(Continued)

(58) Field of Classification Search
CPC ..................... G01N 21/553; G01N 2021/5903; G01N 2201/088; G01N 21/03; G02B 6/10; G02B 6/138; G02B 6/1226; G02B 1/04; G02B 2006/12095
See application file for complete search history.

(56) References Cited

U.S. PATENT DOCUMENTS 5,416,879 A * 5/1995 Liu ..................... G01N 21/0303
356/440
5,570,447 A * 10/1996 Liu ..................... G01N 21/0303
385/125
(Continued)

FOREIGN PATENT DOCUMENTS

EP            0971226 A1     1/2000
JP         2000019100 A      1/2000
(Continued)

OTHER PUBLICATIONS

W. Tsai, Y. Tsao, H. Lin, and B. Sheu, "Cross-point analysis for a multimode fiber sensor based on surface plasmon resonance," Opt. Lett. 30, 2209-2211 (2005).*
(Continued)

*Primary Examiner* — Peter Radkowski
(74) *Attorney, Agent, or Firm* — Alleman Hall McCoy Russell & Tuttle LLP (57) ABSTRACT

There are provided an SPR sensor cell and sensor, both having very excellent detection sensitivity. The SPR sensor cell includes: an under-cladding layer; a core layer, at least a part of the core layer being adjacent to the under-cladding layer; and a metal layer covering the core layer. The core layer includes a uniform layer and a gradient layer arranged between the uniform layer and the under-cladding layer; a refractive index $N_{CO}$ of the uniform layer satisfies a relationship of $1.34 \leq N_{CO} < 1.44$; a refractive index $N_{CL}$ of the under-cladding layer and the refractive index $N_{CO}$ of the (Continued)

uniform layer satisfy a relationship of $N_{CO}-N_{CL} \geq 0.020$; and a refractive index of the gradient layer gradually increases from an under-cladding layer side to a uniform layer side in a thickness direction of the gradient layer within a range of from more than the $N_{CL}$ to less than the $N_{CO}$.

6 Claims, 4 Drawing Sheets

(51) Int. Cl.
| | |
|---|---|
| *G02B 6/10* | (2006.01) |
| *G02B 6/122* | (2006.01) |
| *G02B 6/138* | (2006.01) |
| *G01N 21/59* | (2006.01) |
| *G02B 1/04* | (2006.01) |
| *G02B 6/12* | (2006.01) |

(52) U.S. Cl.
CPC ....... *G02B 6/138* (2013.01); *G01N 2021/5903* (2013.01); *G01N 2201/088* (2013.01); *G02B 1/04* (2013.01); *G02B 2006/12095* (2013.01)

(56) References Cited

U.S. PATENT DOCUMENTS

| | | | | |
|---|---|---|---|---|
| 6,277,330 | B1* | 8/2001 | Liu | G01N 21/552 422/82.05 |
| 6,432,364 | B1* | 8/2002 | Negami | G01N 21/553 385/12 |
| 6,483,959 | B1* | 11/2002 | Singh | G01N 21/0303 385/12 |
| 6,798,521 | B2* | 9/2004 | Elkind | G01N 21/553 356/445 |
| 7,181,096 | B2* | 2/2007 | Matsumoto | G01N 21/7703 250/227.14 |
| 7,221,456 | B2* | 5/2007 | Kanai | G01N 21/553 356/445 |
| 7,469,076 | B2* | 12/2008 | Carlson | C12Q 1/6804 385/12 |
| 7,541,573 | B2* | 6/2009 | Emmerson | G01N 21/4133 250/227.18 |
| 7,697,796 | B2* | 4/2010 | Kashyap | G01N 21/553 385/12 |
| 7,715,005 | B2* | 5/2010 | Emmerson | G01N 21/774 356/328 |
| 2003/0132406 | A1* | 7/2003 | Waldhausl | G01N 21/253 250/574 |
| 2005/0095698 | A1* | 5/2005 | Carlson | C12Q 1/6804 435/287.2 |
| 2005/0117158 | A1* | 6/2005 | Kanai | G01N 21/553 356/445 |
| 2006/0003372 | A1* | 1/2006 | Li | G01N 21/27 435/6.19 |
| 2006/0093262 | A1* | 5/2006 | Matsumoto | G01N 21/7703 385/31 |
| 2008/0043242 | A1* | 2/2008 | Emmerson | G01N 21/4133 356/477 |
| 2008/0204747 | A1* | 8/2008 | Emmerson | G01N 21/774 356/328 |
| 2008/0267555 | A1* | 10/2008 | Kashyap | G01N 21/553 385/12 |
| 2009/0149345 | A1* | 6/2009 | Nishi | B01L 3/502707 506/12 |
| 2010/0133102 | A1* | 6/2010 | Carlson | C12Q 1/6804 204/403.15 |
| 2010/0149540 | A1* | 6/2010 | Boukherroub | C23C 16/0281 356/445 |

FOREIGN PATENT DOCUMENTS

| | | |
|---|---|---|
| JP | 2008242441 A | 10/2008 |
| JP | 2012107902 A | 6/2012 |
| WO | 2008075578 A1 | 6/2008 |

OTHER PUBLICATIONS

Abdelghani A., Jaffrezic-Renault N. SPR fibre sensor sensitised by fluorosiloxane polymers. Sens. Actuators B. 2001;74:117-123.*

ISA Japanese Patent Office, International Search Report Issued in Application No. PCT/JP2013/073251, Sep. 24, 2013, WIPO, 4 pages.

State Intellectual Property Office of the People's Republic of China, First Office Action Issued in Chinese Patent Application No. 201380049550.6, May 25, 2016, 14 pages.

* cited by examiner

SPR SENSOR CELL AND SPR SENSOR

TECHNICAL FIELD

The present invention relates to an SPR sensor cell and an SPR sensor. More specifically, the present invention relates to an SPR sensor cell including an optical waveguide and an SPR sensor.

BACKGROUND ART

Hitherto, in the fields of chemical analysis, biochemical analysis, and the like, a surface plasmon resonance (SPR) sensor including an optical fiber has been used. In the SPR sensor including an optical fiber, a metal thin film is formed on an outer circumferential surface of a tip end portion of the optical fiber, and an analysis sample is fixed to the optical fiber into which light is guided. Among the light to be guided, light having a particular wavelength generates surface plasmon resonance in the metal thin film, and light intensity thereof is attenuated. In such an SPR sensor, the wavelength of the light generating surface plasmon resonance generally varies depending on a refractive index of an analysis sample to be fixed to the optical fiber. Therefore, if a wavelength at which light intensity is attenuated after the generation of surface plasmon resonance is measured, the wavelength of the light generating surface plasmon resonance can be identified. Further, if a change in the wavelength at which light intensity is attenuated is detected, it can be confirmed that the wavelength of the light generating surface plasmon resonance has changed, and hence a change in refractive index of the analysis sample can be confirmed. As a result, such an SPR sensor can be used for various chemical analyses and biochemical analyses such as measurement of a sample concentration and detection of an immunoreaction.

For example, in a case where the sample is a solution, the refractive index of the sample (solution) depends on a concentration of the solution. Therefore, the concentration of the sample can be detected by measuring the refractive index of the sample (solution) with the SPR sensor in which the sample (solution) is in contact with the metal thin film, and further, it can be confirmed that the concentration of the sample (solution) has changed by confirming a change in the refractive index. In an analysis of an immunoreaction, for example, an antibody is fixed onto the metal thin film of the optical fiber in the SPR sensor through intermediation of a dielectric film, an analyte is brought into contact with the antibody, and surface plasmon resonance is generated. In this case, if the antibody and the analyte perform an immunoreaction, the refractive index of the sample changes. Therefore, it can be determined that the antibody and the analyte have performed an immunoreaction by confirming that the refractive index of the sample has changed before and after the contact between the antibody and the analyte.

In the SPR sensor including an optical fiber, the tip end portion of the optical fiber has a fine cylindrical shape, and hence there is a problem in that it is difficult to form the metal thin film and fix an analysis sample to the optical fiber. In order to solve the problem, for example, there has been proposed an SPR sensor cell including a core through which light is transmitted and a clad covering the core, in which a through-hole extending to a surface of the core is formed at a predetermined position of the clad, and a metal thin film is formed on the surface of the core at a position corresponding to the through-hole (see, for example, Patent Literature 1). In such an SPR sensor cell, it is easy to form the metal thin film for generating surface plasmon resonance on the surface of the core and fix the analysis sample onto the surface.

However, in recent years, there is an increasing demand for detection of a minute change and/or a trace amount of component, and thus further enhancement of the detection sensitivity of the SPR sensor cell is being demanded in chemical and biochemical analyses.

CITATION LIST

Patent Literature

[PTL 1] JP 2000-19100 A

SUMMARY OF INVENTION

Technical Problem

The present invention has been made in view of solving the conventional problem, and an object of the present invention is to provide an SPR sensor cell and an SPR sensor, both having very excellent detection sensitivity.

Solution to the Problem

An SPR sensor cell according to an embodiment of the present invention includes: an under-cladding layer; a core layer, at least a part of the core layer being adjacent to the under-cladding layer; and a metal layer covering the core layer. The core layer includes a uniform layer and a gradient layer arranged between the uniform layer and the under-cladding layer; a refractive index $N_{CO}$ of the uniform layer satisfies a relationship of $1.34 \leq N_{CO} < 1.44$; a refractive index $N_{CL}$ of the under-cladding layer and the refractive index $N_{CO}$ of the uniform layer satisfy a relationship of $N_{CO} - N_{CL} \geq 0.020$; and a refractive index of the gradient layer gradually increases from an under-cladding layer side to a uniform layer side in a thickness direction of the gradient layer within a range from more than $N_{CL}$ to less than $N_{CO}$.

In one embodiment of the present invention, the refractive index $N_{CL}$ of the under-cladding layer satisfies a relationship of $1.32 \leq N_{CO} < 1.42$.

In one embodiment of the present invention, the uniform layer contains 35 wt % or more of a halogen. In one embodiment of the present invention, the halogen includes fluorine.

According to another aspect of the present invention, there is provided an SPR sensor. The SPR sensor includes the SPR sensor cell as described above.

Advantageous Effects of the Invention

According to embodiments of the present invention, the SPR sensor cell and the SPR sensor, each having extremely excellent detection sensitivity, are provided by forming the layer having a refractive index gradient in the core layer.

DESCRIPTION OF EMBODIMENTS

A. SPR Sensor Cell

Figure 1:
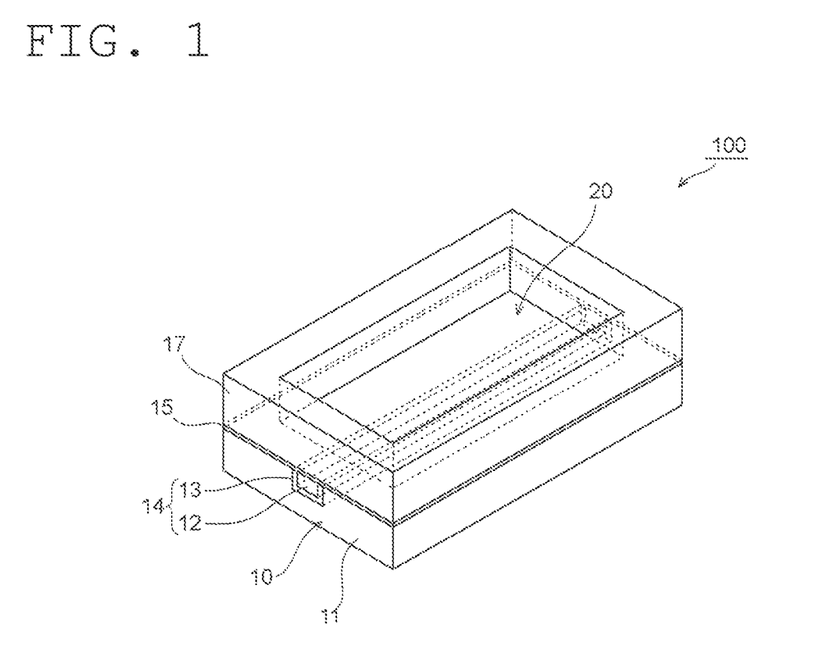
FIG. 1 is a schematic perspective view illustrating an SPR sensor cell according to a preferred embodiment of the present invention.
Figure 2:
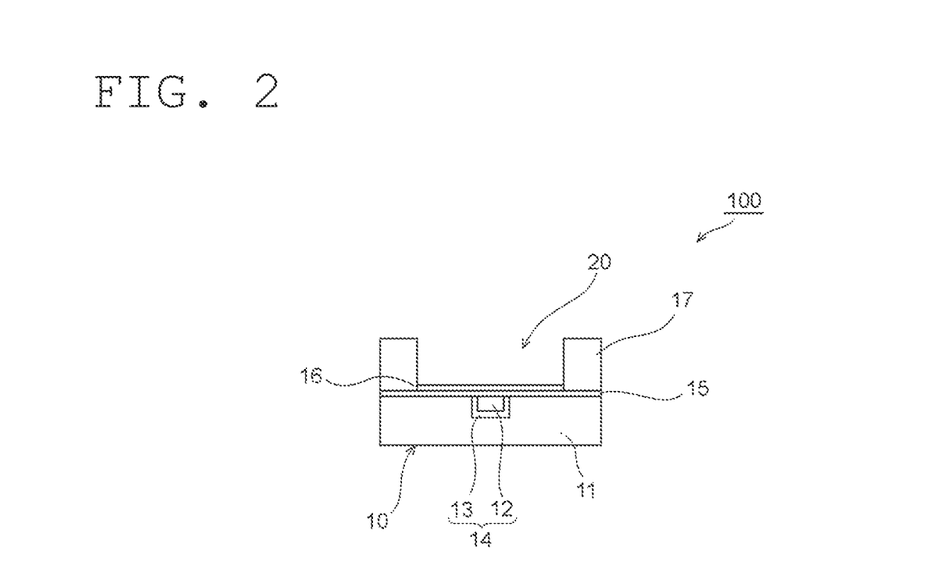
FIG. 2 is a schematic sectional view of the SPR sensor cell illustrated in FIG. 1.

FIG. 1 is a schematic perspective view illustrating an SPR sensor cell according to a preferred embodiment of the present invention. FIG. 2 is a schematic sectional view of the SPR sensor cell illustrated in FIG. 1. It should be noted that, when a direction is mentioned in the following description of the SPR sensor cell, an upper side of the drawing is defined as an upper side, and a lower side of the drawing is defined as a lower side.

As illustrated in FIG. 1 and FIG. 2, an SPR sensor cell 100 is formed in the shape of a bottomed frame having a substantially rectangular shape in a plan view, and includes: an under-cladding layer 11; a core layer 14 including a uniform layer 12 and a gradient layer 13, at least a part of the core layer 14 being adjacent to the under-cladding layer 11; a protective layer 15 covering the upper surface of each of the under-cladding layer 11 and the core layer 14; and a metal layer 16 formed on the protective layer 15 and covering the core layer 14. In the SPR sensor cell 100, the under-cladding layer 11, the core layer 14, the protective layer 15, and the metal layer 16 constitute an optical waveguide and function as a detection unit 10 for detecting the state of a sample and/or a change therein. In a practical case, the SPR sensor cell 100 includes a sample mounting portion 20 provided so as to be adjacent to the detection unit 10. The sample mounting portion 20 is defined by an over-cladding layer 17. The protective layer 15 may be omitted depending on the purpose of use. The over-cladding layer 17 may also be omitted as long as the sample mounting portion 20 can be provided appropriately. In the sample mounting portion 20, a sample (for example, a solution or powder) to be analyzed is mounted so as to come into contact with the detection unit (substantially the metal layer).

The under-cladding layer 11 is formed in the shape of a plate having a substantially rectangular shape in a plan view, with a predetermined thickness. The thickness of the under-cladding layer (thickness from an upper surface of the core layer) is, for example, from 5 μm to 400 μm.

The refractive index of the under-cladding layer 11 (hereinafter sometimes referred to as "$N_{CL}$") is preferably less than 1.42, more preferably 1.39 or less, still more preferably 1.37 or less. In addition, the lower limit of the refractive index of the under-cladding layer is preferably 1.32 or more. When the refractive index of the under-cladding layer falls within such range, a refractive index difference between the under-cladding layer and the uniform layer to be described later can be adjusted to fall within a desired range. As a result, detection sensitivity and an S/N ratio can be improved. It should be noted that the term "refractive index" as used herein means a refractive index at a wavelength of 830 nm.

The core layer 14 is formed substantially in a square column shape (more specifically, a rectangular shape in a cross-section flattened in a width direction) extending in a direction perpendicular to both a width direction (right and left direction of the drawing surface of FIG. 2) and a thickness direction of the under-cladding layer 11, and is buried in an upper end portion substantially at the center of the width direction of the under-cladding layer 11. The direction in which the core layer 14 extends serves as a direction in which light propagates in the optical waveguide. The thickness of the core layer is, for example, from 5 μm to 200 μm, and the width of the core layer is, for example, from 5 μm to 200 μm.

The core layer 14 is arranged so that the upper surface thereof is exposed from the under-cladding layer 11. It is preferred that the core layer 14 be arranged so that the upper surface thereof is flush with an upper surface of the under-cladding layer 11. The metal layer 16 can be arranged efficiently only on an upper side of the core layer by arranging the core layer so that the upper surface thereof is flush with the upper surface of the under-cladding layer. Further, the core layer 14 is arranged so that both end surfaces thereof in the extending direction are flush with both end surfaces of the under-cladding layer in the extending direction.

The core layer 14 includes the uniform layer 12 and the gradient layer 13. The gradient layer 13 is arranged between the uniform layer 12 and the under-cladding layer 11 so as to separate the uniform layer 12 and the under-cladding layer 11.

The refractive index of the uniform layer 12 (hereinafter sometimes referred to as "$N_{CO}$") is less than 1.44, preferably 1.41 or less, more preferably 1.39 or less. When the refractive index of the uniform layer is set to less than 1.44, the detection sensitivity can be markedly improved. The lower limit of the refractive index of the uniform layer is preferably 1.34. When the refractive index of the uniform layer is 1.34 or more, SPR can be excited even in an aqueous solution-based sample (refractive index of water: 1.33), and a general-purpose material can be used.

The refractive index of the uniform layer 12 is higher than that of the under-cladding layer 11. The difference ($N_{CO}-N_{CL}$) between the refractive index of the uniform layer and the refractive index of the under-cladding layer is preferably 0.020 or more, more preferably 0.030 or more. When the difference between the refractive index of the uniform layer and the refractive index of the under-cladding layer falls within such range, the optical waveguide of the detection unit can be set to a so-called multimode. Thus, the amount of light transmitted through the optical waveguide can be increased, and as a result, the S/N ratio can be improved. In addition, the amount of light contributing to SPR excitation in the upper surface of the uniform layer can be sufficiently increased to improve the detection sensitivity.

The uniform layer 12 preferably contains a halogen. When the uniform layer contains a halogen, its refractive index can be adjusted to fall within the above-mentioned range. As a result, the detection sensitivity can be markedly improved. Examples of a halogen include fluorine, chlorine, bromine, and iodine. Of these, fluorine is preferred. This is because fluorine facilitates the adjustment of the refractive index of the uniform layer to a desired refractive index.

Any appropriate means may be adopted as means for incorporating a halogen into the uniform layer 12. Specifically, it is appropriate to form the uniform layer through the use of a halogen-containing material. Examples of a halogen-containing material capable of forming the uniform layer include a halogen atom-containing resin and a halogen compound-containing resin composition. Specific examples of a halogen atom-containing resin include: fluorine atom-containing resins such as polytetrafluoroethylene, a tetrafluoroethylene-hexafluoropropylene copolymer, a fluorinated epoxy resin, a fluorinated polyimide resin, a fluorinated polyamide resin, a fluorinated acrylic resin, a fluorinated polyurethane resin, and a fluorinated siloxane resin; chlorine atom-containing resins such as a vinyl chloride resin, a vinyl chloride-ethylene copolymer, and a chlorinated polyolefin resin; and modified products thereof. Of these, a fluorine atom-containing resin is preferred. The use of a fluorine atom-containing resin can decrease the refractive index of the uniform layer to improve the sensitivity, and can suppress an associated decrease of the S/N ratio. A more specific description is given below. As described above, the use of fluorine can decrease the refractive index of the uniform layer to improve the sensitivity. Meanwhile, when the sensitivity is improved by decreasing the refractive index of the uniform layer, an SPR absorption peak is shifted to a longer wavelength (near-infrared region). In the near-infrared region, C-H vibration absorption is present, and the intensity of light at an excitation wavelength decreases due to the absorption. As a result, the S/N ratio may decrease or may be affected by a waveguide mode. When a fluorine atom, which is heavier than a hydrogen atom, is bonded to carbon, the vibration absorption can be shifted to a longer wavelength, and a decrease of the light intensity can be suppressed. Accordingly, a decrease of the S/N ratio can be suppressed. An example of a halogen compound-containing resin composition is a resin composition containing a halogen compound and an epoxy resin, a polyimide resin, a polyamide resin, a silicone resin, an acrylic resin, and/or a urethane resin. Specific examples of a halogen compound include hexabromobenzene, hexachlorobenzene, pentabromobenzene, pentachlorobenzene, pentabromophenol, pentachlorophenol, hexabromobiphenyl, decabromobiphenyl, chlorotetrabromobutane, tetrabromobutane, hexabromocyclododecane, perchloropentacyclodecane, decabromodiphenyl ether, octabromodiphenyl ether, hexabromodiphenyl ether, ethylenebis-tetrabromophthalimide, tetrachlorobisphenol A, tetrabromobisphenol A, brominated polystyrene, halogenated polycarbonate, a halogenated epoxy compound, brominatedpolyphenylene oxide, polychlorostyrene, chlorinated paraffin, tetrabromophthalic anhydride, and tetrachlorophthalic anhydride. A halogen-containing material (material for forming the uniform layer) may be preferably used as a photosensitive material by being blended with a photosensitizer.

The halogen content of the uniform layer 12 (substantially the material for forming the uniform layer) is preferably 35 wt % or more, more preferably 40 wt % or more, and still more preferably 50 wt % or more. When the halogen content falls within such a range, a uniform layer having a desired refractive index can be obtained. As a result, an SPR sensor cell having extremely excellent detection sensitivity can be obtained. On the other hand, the upper limit of the halogen content is preferably 78 wt %. When the upper limit is more than 78 wt %, the uniform layer may liquefy or gasify to make it impossible to maintain the shape of the uniform layer in some cases.

The gradient layer 13 has a refractive index that gradually increases from the under-cladding layer 11 side to the uniform layer 12 side in the thickness direction of the gradient layer 13 within the range from more than the refractive index $N_{CL}$ of the under-cladding layer to less than the refractive index $N_{CO}$ of the uniform layer. The refractive index may increase in a stepwise manner, but preferably increases in a continuous manner from the viewpoint of reducing a propagation loss. Specifically, from an interface region between the under-cladding layer and the gradient layer to an interface region between the gradient layer and the uniform layer in the thickness direction of the gradient layer, the refractive index increases from $N_{CL}$ to $N_{CO}$ in a continuous manner or in a stepwise manner, preferably in a continuous manner. The use of a gradient layer having such a refractive index allows incident light that propagates in the gradient layer to be guided to the uniform layer. As a result, the amount of light contributing to SPR excitation is increased to promote SPR excitation, and hence the detection sensitivity can be improved.

In one embodiment, the gradient layer 13 may have, in its thickness direction, a gradient structure such as a composition gradient, a concentration gradient, or a cross-linking density gradient. When the gradient layer 13 has a gradient structure, a refractive index that gradually increases toward the above-mentioned predetermined direction in the thickness direction of the gradient layer 13 can be suitably realized.

The thickness of each of the uniform layer 12 and the gradient layer 13 may be set to any appropriate value depending on, for example, the purpose of use. For example, in an SPR sensor of the present invention, the refractive index difference between the under-cladding layer and the uniform layer is set to a predetermined value or higher. Accordingly, by decreasing the thickness of the uniform layer and increasing the thickness of the gradient layer, the gradient of a refractive index distribution from the upper surface of the core layer to its bottom surface can be increased to efficiently condense incident light in the vicinity of the metal layer 16. As a result, SPR excitation is suitably promoted, and hence excellent detection sensitivity can be obtained.

The material for forming the uniform layer 12 is as described above. Any appropriate material may be used as a material for forming the under-cladding layer 11 as long as the above-mentioned refractive index is obtained. For example, the under-cladding layer may be formed from a material that is similar to the material for forming the uniform layer, but that is adjusted so as to have a lower refractive index than the core layer (uniform layer and gradient layer).

The gradient layer 13 may be formed through the use of any appropriate material as long as the above-mentioned refractive index is obtained. For example, the gradient layer 13 may be formed by impregnating the surface layer of the uniform layer formed in advance with the material for forming the under-cladding layer so as to generate a composition gradient (that is, so that the composition may change in a continuous manner) in the thickness direction of the gradient layer 13. In addition, for example, the gradient layer 13 may be formed by using the same material as the material for forming the uniform layer and generating a concentration gradient or a cross-linking density gradient in the thickness direction of the gradient layer 13. Alternatively, the gradient layer 13 may be formed by, for example, sequentially laminating a plurality of materials, each having a higher refractive index than the material for forming the under-cladding layer and a lower refractive index than the material for forming the uniform layer so as to generate a refractive index gradient.

The protective layer 15 is formed as a thin film in the same shape as that of the under-cladding layer in a plan view so as to cover all the upper surfaces of the under-cladding layer 11 and the core layer 14, as required. By forming the protective layer 15, for example, in a case where the sample is a liquid, the core layer and/or the cladding layer can be prevented from being swollen with the sample. As a material for forming the protective layer 15, examples may include titanium dioxide, silicon dioxide, and aluminum oxide. The thickness of the protective layer 15 is preferably from 1 nm to 100 nm, more preferably from 5 nm to 20 nm.

As illustrated in FIG. 2, the metal layer 16 is formed so as to uniformly cover the upper surface of the core layer 14 through intermediation of the protective layer 15. In this case, as required, an easy-adhesion layer (not shown) may be formed between the protective layer 15 and the metal layer 16. By forming the easy-adhesion layer, the protective layer 15 and the metal layer 16 can be firmly fixed to each other. The core layer 14 may be directly covered with the metal layer 16 without forming the protective layer 15.

As a material for forming the metal layer 16, examples include gold, silver, platinum, copper, aluminum, and alloys thereof. The metal layer 16 may be a single layer or may have a laminate structure of two or more layers. The thickness (total thickness of all the layers in the case of the laminate structure) of the metal layer 16 is preferably from 20 nm to 70 nm, more preferably from 30 nm to 60 nm.

As a material for forming the easy-adhesion layer, typical examples include chromium and titanium. The thickness of the easy-adhesion layer is preferably from 1 nm to 5 nm.

As illustrated in FIG. 1, the over-cladding layer 17 is formed in the shape of a frame having a rectangular shape in a plan view so that an outer circumference of the over-cladding layer 17 becomes substantially flush with an outer circumference of the under-cladding layer 11 in a plan view, on the upper surfaces of the under-cladding layer 11 and the core layer 14 (upper surface of the protective layer 15 in the illustrated example). A portion surrounded by the upper surfaces of the under-cladding layer 11 and the core layer 14 (upper surface of the protective layer 15 in the illustrated example) and the over-cladding layer 17 is partitioned as the sample mounting portion 20. By mounting a sample in the partitioned portion, the metal layer of the detection unit 10 and the sample come into contact with each other so that detection can be performed. Further, by forming such a partitioned portion, a sample can be easily mounted on the surface of the metal layer, and hence operability can be enhanced.

As a material for forming the over-cladding layer 17, for example, the materials for forming the core layer and the under-cladding layer, and silicone rubber may be utilized. The thickness of the over-cladding layer is preferably 5 µm to 2,000 µm, more preferably 25 µm to 200 µm. The refractive index of the over-cladding layer is preferably lower than that of the core layer (the uniform layer and the gradient layer). In one embodiment, the refractive index of the over-cladding layer is equal to that of the under-cladding layer. Note that, in the case of forming a protective layer having a refractive index lower than that of the core layer (the uniform layer and the gradient layer), the refractive index of the over-cladding layer is not necessarily required to be lower than that of the core layer.

Although the SPR sensor cell according to the preferred embodiment of the present invention has been described, the present invention is not limited thereto. For example, in the relationship between the core layer and the under-cladding layer, at least a portion of the core layer has only to be adjacent to the under-cladding layer. For example, although a configuration in which the core layer is buried in the under-cladding layer is described in the above-mentioned embodiment, the core layer may be provided so as to pass through the under-cladding layer. Alternatively, the core layer may be formed on the under-cladding layer so that a predetermined portion of the core layer is surrounded by the over-cladding layer.

Figure 3:
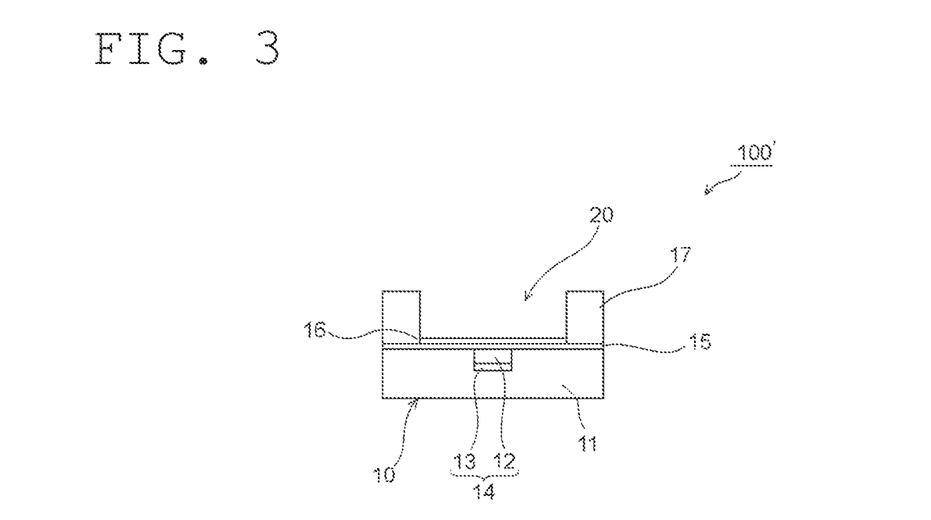
FIG. 3 is a schematic sectional view of an SPR sensor cell according to another preferred embodiment of the present invention.

In addition, for example, in the relationship among the under-cladding layer, the uniform layer, and the gradient layer, the gradient layer only needs to be interposed in at least a part of the region in which the uniform layer and the under-cladding layer are adjacent to each other. For example, as illustrated in FIG. 3, the gradient layer may be formed only between the bottom surface of the uniform layer and the under-cladding layer.

Further, the number of core layers in the SPR sensor cell may be changed depending on the purpose of use. Specifically, a plurality of the core layers may be formed at a predetermined interval in the width direction of the under-cladding layer. With such a configuration, a plurality of samples can be analyzed simultaneously, and hence analysis efficiency can be enhanced. As the shape of the core layer, any suitable shape (for example, a semicircular column shape or a convex column shape) can be adopted depending on the purpose of use.

Further, a lid may be provided on an upper portion of the SPR sensor cell 100 (sample mounting portion 20). With such a configuration, a sample can be prevented from coming into contact with ambient air. Further, in a case where the sample is a solution, a change in concentration caused by evaporation of a solvent can be prevented. In a case of providing a lid, an injection port for injecting a liquid sample into the sample mounting portion and a discharge port for discharging the liquid sample from the sample mounting portion may be provided. With such a configuration, the sample can be allowed to flow and to be supplied to the sample mounting portion continuously, and hence the characteristics of the sample can be measured continuously.

The above-mentioned embodiments may be combined appropriately.

B. Method of Manufacturing SPR Sensor Cell

The SPR sensor cell of the present invention may be manufactured by any appropriate method. FIGS. 4A to 4K are schematic sectional views illustrating an example of a method of manufacturing the SPR sensor cell of the present invention.

Figure 4A:
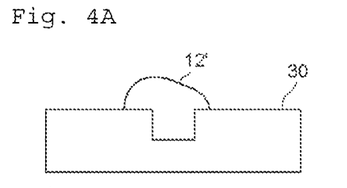
FIGS. 4A to 4K are schematic sectional views illustrating an example of a method of manufacturing an SPR sensor cell of the present invention.
Figure 4B:
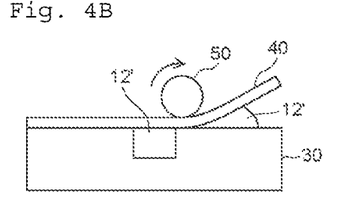
Figure 4C:
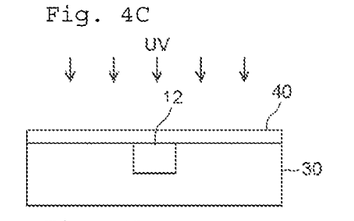
Figure 4D:
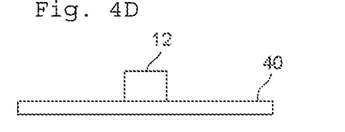

First, as illustrated in FIG. 4A, a material 12' for forming the uniform layer is arranged on the surface of a mold 30 having a recess corresponding to the shape of the core layer. Then, as illustrated in FIG. 4B, a transfer film 40 is attached onto the surface of the mold 30 while being pressed through the use of pressing means 50 in a predetermined direction to fill the recess with the material 12' for forming the uniform layer, and at the same time, to remove an excess of the material 12' for forming the uniform layer. After that, as illustrated in FIG. 4C, the material 12' for forming the uniform layer filled into the recess is irradiated with UV light to cure the material, to thereby form the uniform layer 12. UV irradiation conditions may be appropriately set depending on the kind of the material for forming the uniform layer. As required, the material for forming the uniform layer may be heated. The heating may be performed before the UV irradiation, may be performed after the UV irradiation, or may be performed simultaneously with the UV irradiation. Heating conditions may be appropriately set depending on the kind of the material for forming the uniform layer. Further, as illustrated in FIG. 4D, the transfer film 40 is peeled from the mold 30 to transfer the uniform layer 12 onto the transfer film 40.

Figure 4E:
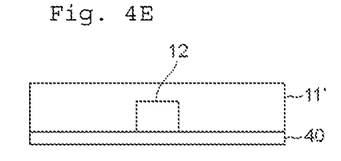
Figure 4F:
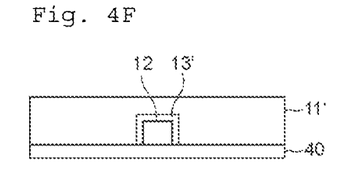
Figure 4G:
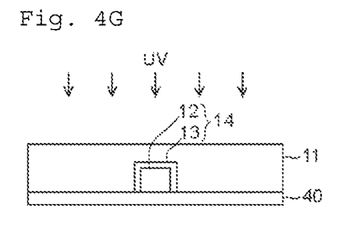
Figure 4H:
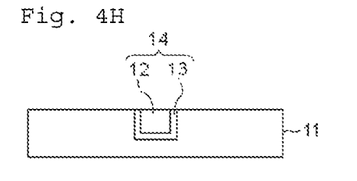

Next, as illustrated in FIG. 4E, a material 11' for forming the under-cladding layer is applied so as to cover the uniform layer 12. Alternatively, the material 11' for forming the under-cladding layer may be applied in advance onto another support (for example, a corona-treated PET film), followed by the attachment of the support and the transfer film 40 onto each other so that the material 11' for forming the under-cladding layer may cover the uniform layer 12. After that, as illustrated in FIG. 4F, the applied material 11' for forming the under-cladding layer is heated to impregnate the surface layer of the uniform layer 12 with a part of the material for forming the under-cladding layer. At this time, the region impregnated with the material for forming the under-cladding layer is a region 13' to be converted into the gradient layer 13. A heating temperature and a heating time may be appropriately set depending on, for example, the kind of the material for forming the under-cladding layer. The heating temperature is, for example, from 40° C. to 200° C., preferably from 40° C. to 120° C. The heating time is, for example, from 10 seconds to 180 minutes, preferably from 5 minutes to 120 minutes. The amount of the material for forming the under-cladding layer with which the uniform layer is impregnated tends to increase when the heating temperature is increased or the heating time is increased. Accordingly, the thicknesses of the uniform layer and the gradient layer can be adjusted by adjusting the heating temperature and/or the heating time. Next, as illustrated in FIG. 4G, the material 11' for forming the under-cladding layer is irradiated with UV light to cure the material, to thereby form the under-cladding layer 11 and the gradient layer 13. UV irradiation conditions may be appropriately set depending on the kind of the material for forming the under-cladding layer. After that, as illustrated in FIG. 4H, the transfer film 40 is peeled off and removed.

Figure 4I:
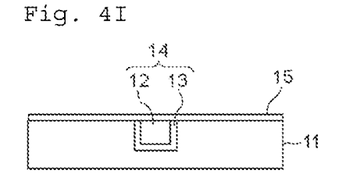

As required, as illustrated in FIG. 4I, the protective layer 15 is formed on the under-cladding layer 11 and the core layer 14. The protective layer is formed, for example, by subjecting a material for forming a protective layer to sputtering or vapor deposition. In a case of forming the protective layer, it is preferred that an easy-adhesion layer (not shown) be formed on the protective layer. The easy-adhesion layer is formed, for example, by subjecting chromium or titanium to sputtering.

Figure 4J:
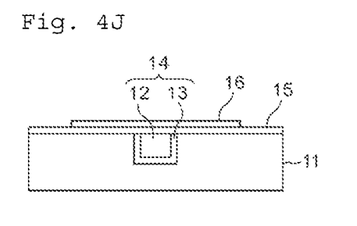

Next, as illustrated in FIG. 4J, the metal layer 16 is formed on the protective layer 15 (upper surfaces of the core layer and the under-cladding layer in a case where the protective layer is not formed) so as to cover the core layer 14. Specifically, the metal layer 16 is formed, for example, by subjecting a material for forming a metal layer to vacuum deposition, ion plating, or sputtering through a mask having a predetermined pattern.

Figure 4K:
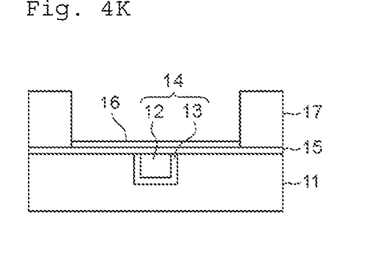

Finally, as illustrated in FIG. 4K, the over-cladding layer 17 having a predetermined frame shape is formed. The over-cladding layer 17 may be formed by any appropriate method. The over-cladding layer 17 may be formed, for example, by arranging a mold having a predetermined frame shape on the protective layer 15, filling the mold with varnish of a material for forming an over-cladding layer, drying the varnish, curing the varnish as required, and finally removing the mold. In a case of using a photosensitive material, the over-cladding layer 17 may be formed by applying the varnish over the entire surface of the protective layer 15, drying the varnish, and then exposing the varnish to light through a photomask having a predetermined pattern, followed by development.

As described above, the SPR sensor cell illustrated in FIG. 1 can be produced.

C. SPR Sensor

Figure 5:
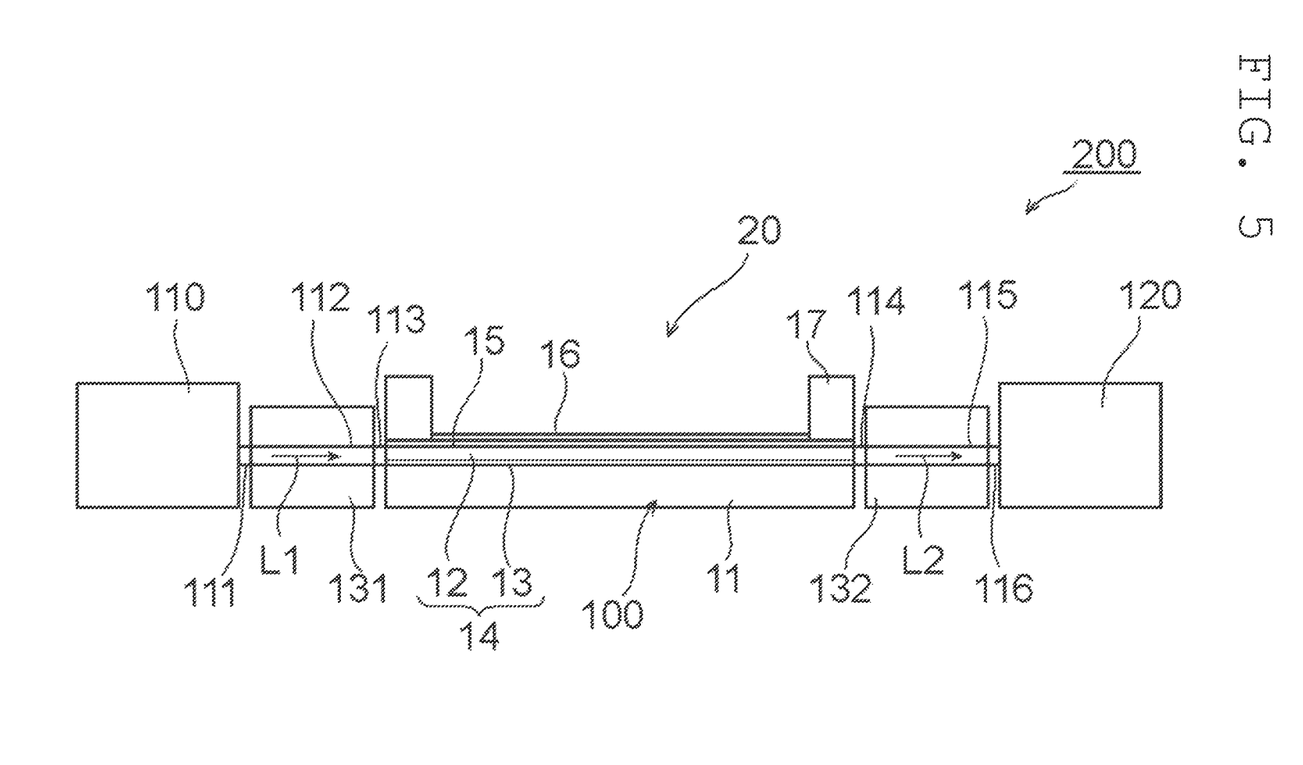
FIG. 5 is a schematic sectional view illustrating an SPR sensor according to a preferred embodiment of the present invention.

FIG. 5 is a schematic sectional view illustrating an SPR sensor according to a preferred embodiment of the present invention. An SPR sensor 200 includes the SPR sensor cell 100, a light source 110, and an optical measuring instrument 120. The SPR sensor cell 100 is the SPR sensor cell of the present invention described in the above-mentioned sections A and B.

As the light source 110, any suitable light source can be adopted. Specific examples of the light source include a white light source and a monochromatic light source. The optical measuring instrument 120 is connected to any suitable arithmetic processing device, and enables accumulation, display and processing of data.

The light source 110 is connected to a light source side optical fiber 112 through a light source side optical connector 111. The light source side optical fiber 112 is connected to one side end portion in a propagation direction of the SPR sensor cell 100 (core layer 14) through a light source side fiber block 113. A measuring instrument side optical fiber 115 is connected to the other side end portion in the propagation direction of the SPR sensor cell 100 (core layer 14) through a measuring instrument side fiber block 114. The measuring instrument side optical fiber 115 is connected to the optical measuring instrument 120 through a measuring instrument side optical connector 116.

The SPR sensor cell 100 is fixed by any suitable sensor cell fixing device (not shown). The sensor cell fixing device is movable in a predetermined direction (for example, a width direction of the SPR sensor cell), and thus the SPR sensor cell can be disposed at a desired position.

The light source side optical fiber 112 is fixed by a light source side optical fiber fixing device 131, and the measuring instrument side optical fiber 115 is fixed by a measuring instrument side optical fiber fixing device 132. The light source side optical fiber fixing device 131 and the measuring instrument side optical fiber fixing device 132 are each fixed to any suitable six-axis movable stage (not shown) so as to be movable in the propagation direction of the optical fiber, width direction (direction orthogonal to the propagation direction in a horizontal direction) and thickness direction (direction orthogonal to the propagation direction in a perpendicular direction), and rotatable about axes in the above-mentioned respective directions.

In the SPR sensor as described above, the light source 110, the light source side optical fiber 112, the SPR sensor cell 100 (core layer 14), the measuring instrument side optical fiber 115, and the optical measuring instrument 120 can be arranged on one axis, and light can be guided from the light source 110 so as to be transmitted therethrough.

An example of the manner of use of such an SPR sensor is described below.

First, a sample is mounted on the sample mounting portion 20 of the SPR sensor cell 100, and the sample and the metal layer 16 are brought into contact with each other. Then, predetermined light from the light source 110 is guided to the SPR sensor cell 100 (core layer 14) through the light source side optical fiber 112 (see arrow L1 of FIG. 5). The light guided to the SPR sensor cell 100 (core layer 14) is transmitted through the SPR sensor cell 100 (core layer 14) while light that propagates in the gradient layer 13 is condensed into the uniform layer 12 and total reflection is repeated, and part of the light enters the metal layer 16 on an upper surface of the core layer 14 (uniform layer 12) and is attenuated by surface plasmon resonance. The light transmitted through the SPR sensor cell 100 (core layer 14) is guided to the optical measuring instrument 120 through the measuring instrument side optical fiber 115 (see arrow L2 of FIG. 5). That is, in the SPR sensor 200, the intensity of light having a wavelength generating surface plasmon resonance in the core layer 14 (uniform layer 12) is attenuated in the light guided to the optical measuring instrument 120. The wavelength of light generating surface plasmon resonance depends on, for example, the refractive index of the sample brought into contact with the metal layer 16. Therefore, by detecting the attenuation of the light intensity of the light guided to the optical measuring instrument 120, a change in refractive index of the sample can be detected.

For example, in a case of using a white light source as the light source 110, a change in refractive index of the sample can be confirmed by measuring the wavelength of light whose light intensity is attenuated after transmission through the SPR sensor cell 100 (wavelength of light generating surface plasmon resonance) with the optical measuring instrument 120 and detecting a change in wavelength of the light whose light intensity is attenuated. Further, for example, in a case of using a monochromatic light source as the light source 110, a change in wavelength of light generating surface plasmon resonance can be confirmed and a change in refractive index of the sample can be confirmed by measuring a change (attenuation degree) in light intensity of monochromatic light after transmission through the SPR sensor cell 100 with the optical measuring instrument 120 and detecting a change in attenuation degree.

As described above, such an SPR sensor cell can be used, for example, for various chemical and biochemical analyses such as the measurement of a sample concentration and the detection of an immunoreaction, based on a change in refractive index of the sample. More specifically, for example, in a case where the sample is a solution, the refractive index of the sample (solution) depends on the concentration of the solution, and hence the concentration of the sample can be measured by detecting the refractive index of the sample. Further, a change in the concentration of the sample can be confirmed by detecting a change in the refractive index of the sample. Further, for example, in the detection of an immunoreaction, an antibody is fixed onto the metal layer 16 of the SPR sensor cell 100 through intermediation of a dielectric film, and an analyte is brought into contact with the antibody. If the antibody and the analyte perform an immunoreaction, the refractive index of the sample changes. Therefore, it can be determined that the antibody and the analyte have performed an immunoreaction by detecting a change in the refractive index of the sample before and after contact between the antibody and the analyte.

EXAMPLES

The present invention is hereinafter described specifically by way of Examples. However, the present invention is not limited thereto. It should be noted that measurement methods used in the Examples and Comparative Examples are as described below.

<Refractive Index>

A refractive index was measured as follows: a film having a thickness of 10 μm was formed on a silicon wafer, and the refractive index of the film was measured at a wavelength of 830 nm with a prism coupler-type refractive index measurement apparatus.

<Fluorine Content>

A fluorine content was measured as follows: a weighed sample was burned with an automatic sample combustion apparatus to generate a gas, which was collected in 10 mL of an absorbent liquid, and the absorbent liquid was subjected to quantitative analysis with an ion chromatograph (IC).

Example 1

An SPR sensor cell was produced by a manufacturing method as illustrated in FIG. 4A to FIG. 4K. Specifically, a material for forming a uniform layer was dropped onto a surface of a mold (length: 200 mm, width: 200 mm) having formed in the surface a recess for core layer formation having a width of 50 μm and a thickness (depth) of 50 μm. One end of the corona-treated surface of a polypropylene (PP) film (thickness: 40 μm) having one surface subjected to corona treatment was brought into abutment with the surface of the mold and the other end was allowed to curve upward. Under this state, while a roller was pressed against the abutment portion between the mold and the PP film from the PP film side, the roller was rolled toward the other end side to attach the mold and the PP film onto each other. Thus, the recess of the mold was filled with the material for forming a uniform layer and an excess of the material for forming a uniform layer was pushed out. Next, the resultant laminate was irradiated with UV light from the PP film side to completely cure the material for forming a uniform layer, to thereby form a uniform layer (refractive index: 1.384, fluorine content: 54 wt %). It should be noted that the material for forming a uniform layer was prepared by stirring and dissolving 60 parts by weight of a fluorine-based UV-curable resin (manufactured by DIC Corporation, trade name: "OP38Z") and 40 parts by weight of a fluorine-based UV-curable resin (manufactured by DIC Corporation, trade name: "OP40Z"). Next, the PP film was peeled from the mold to transfer the uniform layer, which had a substantially square column shape measuring 50 μm in thickness and 50 μm in width, onto the film.

A material for forming an under-cladding layer (fluorine-based UV-curable resin (manufactured by Solvay Specialty Polymers Japan K.K., trade name: "Fluorolink MD700")) was applied onto a corona-treated PET support. Then, the PET support and the PP film were attached onto each other so that the material for forming an under-cladding layer covered the entire outer surface of the uniform layer. It should be noted that the applied thickness of the material for forming an under-cladding layer after the attachment (thickness ranging from the upper surface of the uniform layer to the PET support) was 100 μm. Next, the material for forming an under-cladding layer was heated at 50° C. for 90 minutes. Heat treatment caused the surface layer of the uniform layer to be impregnated with the material for forming an under-cladding layer. Then, the result was irradiated with UV light to cure the material for forming an under-cladding layer, to thereby form an under-cladding layer (refractive index: 1.347) and a gradient layer. After that, the PP film was peeled off and removed, and the under-cladding layer and the core layer were turned upside down. Thus, a buried-type optical waveguide film was produced.

Then, $TiO_2$ was sputtered onto the entire surface of an upper surface (core layer exposed surface) of the optical waveguide film thus obtained to form a protective layer (thickness: 10 nm). The optical waveguide film with the protective layer formed thereon was subjected to dice cutting to a length of 22.25 mm and a width of 20 mm. After that, chromium and silver were sputtered onto the cut optical waveguide film in the stated order through a mask with an opening having a length of 6 mm and a width of 1 mm, and thus an easy-adhesion layer (thickness: 1 nm) and a metal layer (thickness: 30 nm) were formed in the stated order so as to cover the core layer through intermediation of the protective layer. Finally, a frame-shaped over-cladding layer was formed by a method similar to that for forming the under-cladding layer, through use of the same material as that for forming the under-cladding layer. Accordingly, the SPR sensor cell as illustrated in FIGS. 1 and 2 was produced.

The SPR sensor cell obtained as described above, a halogen light source (manufactured by Ocean Optics, Inc., trade name: "HL-2000-HP"), and a spectroscope (manufactured by Ocean Optics, Inc., trade name: "USB4000") were arranged on one axis and connected to each other to produce an SPR sensor as illustrated in FIG. 5. 40 µL each of five kinds of ethylene glycol aqueous solutions of different concentrations (concentration: 1 vol % (refractive index: 1.334), 5 vol % (refractive index: 1.33827), 10 vol % (refractive index: 1.3436), 20 vol % (refractive index: 1.35459), and 30 vol % (refractive index: 1.36527)) were supplied to the sample mounting portion of the SPR sensor cell and subjected to measurement. Further, a transmittance spectrum was determined in a case where light intensity at each wavelength when light was transmitted through the SPR sensor cell (optical waveguide) under the condition that the sample (ethylene glycol aqueous solution) was not mounted was defined as 100%, and the peak intensity of the transmittance spectrum appearing at a specific wavelength was measured. In this case, a larger value for the peak intensity indicates higher detection sensitivity. Table 1 shows the result.

Example 2

An SPR sensor cell and an SPR sensor were produced in the same way as in Example 1 except for: changing the heating time before the UV curing of the material for forming an under-cladding layer to 120 minutes; and forming a uniform layer having a refractive index of 1.399 and a fluorine content of 52 wt % through the use of a fluorine-based UV-curable resin (manufactured by DIC Corporation, trade name: "OP40Z") as the material for forming a uniform layer. The SPR sensor thus obtained was evaluated in the same way as in Example 1. Table 1 shows the result.

Example 3

An SPR sensor cell and an SPR sensor were produced in the same way as in Example 1 except for: forming a uniform layer having a refractive index of 1.399 and a fluorine content of 52 wt % through the use of a fluorine-based UV-curable resin (manufactured by DIC Corporation, trade name: "OP40Z") as the material for forming a uniform layer; and forming an under-cladding layer and an over-cladding layer, each having a refractive index of 1.323 through the use of a fluorine-based UV-curable resin (manufactured by Solvay Specialty Polymers Japan K.K., trade name: "Fluorolink MD500"). The SPR sensor thus obtained was evaluated in the same way as in Example 1. Table 1 shows the result.

Comparative Example 1

An SPR sensor cell and an SPR sensor were produced in the same way as in Example 1 except for not subjecting the material for forming an under-cladding layer before the UV curing to heat treatment (consequently not forming the gradient layer). The SPR sensor thus obtained was evaluated in the same way as in Example 1. Table 1 shows the result.

Comparative Example 2

An SPR sensor cell and an SPR sensor were produced in the same way as in Example 2 except for not subjecting the material for forming an under-cladding layer before the UV curing to heat treatment (consequently not forming the gradient layer). The SPR sensor thus obtained was evaluated in the same way as in Example 1. Table 1 shows the result.

Comparative Example 3

An SPR sensor cell and an SPR sensor were produced in the same way as in Example 3 except for not subjecting the material for forming an under-cladding layer before the UV curing to heat treatment (consequently not forming the gradient layer). The SPR sensor thus obtained was evaluated in the same way as in Example 1. Table 1 shows the result.

Comparative Example 4

An SPR sensor cell and an SPR sensor were produced in the same way as in Example 1 except for: forming an under-cladding layer and an over-cladding layer, each having a refractive index of 1.368, through the use of a material for cladding formation prepared by stirring and dissolving 60 parts by weight of a fluorine-based UV-curable resin (manufactured by Solvay Specialty Polymers Japan K.K., trade name: "Fluorolink MD700") and 40 parts by weight of a fluorine-based UV-curable resin (manufactured by Solvay Specialty Polymers Japan K.K., trade name: "Fluorolink 5101X"); and not subjecting the material for forming an under-cladding layer before the UV curing to heat treatment (consequently not forming the gradient layer). The SPR sensor thus obtained was evaluated in the same way as in Example 1. Table 1 shows the result.

Comparative Example 5

An SPR sensor cell and an SPR sensor were produced in the same way as in Example 1 except for forming an under-cladding layer and an over-cladding layer, each having a refractive index of 1.368 through the use of a material for cladding formation prepared by stirring and dissolving 60 parts by weight of a fluorine-based UV-curable resin (manufactured by Solvay Specialty Polymers Japan K.K., trade name: "Fluorolink MD700") and 40 parts by weight of a fluorine-based UV-curable resin (manufactured by Solvay Specialty Polymers Japan K.K., trade name: "Fluorolink 5101X"). The SPR sensor thus obtained was evaluated in the same way as in Example 1. Table 1 shows the result.

TABLE 1

| | Refractive index of uniform layer ($N_{CO}$) | Refractive index of under-cladding layer ($N_{CL}$) | Refractive index difference ($N_{CO} - N_{CL}$) | Presence or absence of gradient layer | Transmittance spectrum peak intensity |
|---|---|---|---|---|---|
| Example 1 | 1.384 | 1.347 | 0.037 | Present | 40T % |
| Example 2 | 1.399 | 1.347 | 0.052 | Present | 50T % |
| Example 3 | 1.399 | 1.323 | 0.076 | Present | 45T % |
| Comparative Example 1 | 1.384 | 1.347 | 0.037 | Absent | 30T % |

TABLE 1-continued

| | Refractive index of uniform layer ($N_{CO}$) | Refractive index of under-cladding layer ($N_{CL}$) | Refractive index difference ($N_{CO} - N_{CL}$) | Presence or absence of gradient layer | Transmittance spectrum peak intensity |
|---|---|---|---|---|---|
| Comparative Example 2 | 1.399 | 1.347 | 0.052 | Absent | 30T % |
| Comparative Example 3 | 1.399 | 1.323 | 0.076 | Absent | 30T % |
| Comparative Example 4 | 1.384 | 1.368 | 0.016 | Absent | 30T % |
| Comparative Example 5 | 1.384 | 1.368 | 0.016 | Present | 30T % |

<Evaluation>

As is apparent from Table 1, the detection sensitivity of each of the SPR sensor cells of Examples is excellent as compared to the SPR sensor cells of Comparative Examples. Specifically, the detection sensitivity of each of the SPR sensor cells of Examples 1 to 3, including the gradient layer, is more excellent than the detection sensitivity of each of the SPR sensor cells of Comparative Examples 1 to 4 not including the gradient layer. In addition, although the SPR sensor cell of Comparative Example 5 included the gradient layer, no detection sensitivity-improving effect was obtained. This was probably because the condensation of light into the uniform layer was insufficient owing to the small refractive index difference between the uniform layer and the under-cladding layer.

INDUSTRIAL APPLICABILITY

The SPR sensor cell and SPR sensor of the present invention can be used suitably in various chemical and biochemical analyses such as the measurement of a sample concentration and the detection of an immunoreaction.

REFERENCE CHARACTERS LIST 10 detection unit
11 under-cladding layer
12 uniform layer
13 gradient layer
14 core layer
15 protective layer
16 metal layer
17 over-cladding layer
20 sample mounting portion
100 SPR sensor cell
110 light source
120 optical measuring instrument
200 SPR sensor

The invention claimed is:

1. An SPR sensor cell, comprising:
an under-cladding layer having a constant refractive index of $N_{CL}$;
a core layer, at least a part of the core layer being adjacent to the under-cladding layer; and
a metal layer covering the core layer,
wherein:
the core layer includes a uniform layer and a gradient layer arranged between the uniform layer and the under-cladding layer;
a refractive index $N_{CO}$ of the uniform layer is substantially uniform throughout the uniform layer, the refractive index $N_{CO}$ being a value greater than or equal to 1.34 and less than 1.44;
a first interface region between the gradient layer and the uniform layer has a refractive index of $N_{CO}$;
a second interface region between the gradient layer and the under-cladding layer has a refractive index of $N_{CL}$;
a refractive index of the gradient layer increases from the second interface region to the first interface region in a thickness direction of the gradient layer from $N_{CL}$ to $N_{CO}$, a difference between $N_{CO}$ and $N_{CL}$, being equal to or greater than 0.020.

2. The SPR sensor cell according to claim 1, wherein the refractive index $N_{CL}$ of the under-cladding layer is a value greater than or equal to 1.32 and less than 1.42.

3. The SPR sensor cell according to claim 1, wherein the uniform layer contains 35 wt % or more of a halogen.

4. The SPR sensor cell according to claim 3, wherein the halogen comprises fluorine.

5. An SPR sensor, comprising the SPR sensor cell according to claim 1.

6. The SPR sensor cell according to claim 1, wherein the thickness direction is perpendicular to a propagation direction of light in the uniform layer.

* * * * *